United States Patent [19]

Martin

[11] Patent Number: 4,598,156
[45] Date of Patent: Jul. 1, 1986

[54] PROCESS FOR PRODUCING INDOLES UNSUBSTITUTED IN THE 2,3-POSITION AND N(3-CHLOROPROPIONYL)INDOLE PRODUCED THEREBY

[75] Inventor: Pierre Martin, Rheinfelden, Switzerland

[73] Assignee: Ciba Geigy Corporation, Ardsley, N.Y.

[21] Appl. No.: 464,528

[22] Filed: Feb. 7, 1983

[30] Foreign Application Priority Data

Feb. 10, 1982 [CH] Switzerland .......................... 815/82

[51] Int. Cl.[4] ........................................... C07D 209/02
[52] U.S. Cl. ................................... 548/501; 548/427; 548/428; 548/447; 548/508; 546/94; 502/230
[58] Field of Search .................... 548/508, 500, 501

[56] References Cited

FOREIGN PATENT DOCUMENTS

| 0031660 | 3/1978 | Japan | 548/508 |
| 0036451 | 4/1981 | Japan | 548/508 |
| 1394373 | 5/1975 | United Kingdom |  |

OTHER PUBLICATIONS

Johnson et al., J.A.C.S., 71, pp. 1901–1905, 1949.
Madelung, "Uder eine Neve Darstellungsweise für ...," Ber. Deutschen Chem. Ges. 45, 1128–34, (1912).
Gould, Mechanism und Struktur in der Organische Chemie, 517 (1962).
Tóth et al., "Catalytic Hydrogenation of Indole ...", Acta Chim. Acad. Sci. Hung. 67, 229–39, (1971).
Julian et al., "Photoaddition of Ketones to Indoles ...," [1973] J.C.S. Chem. Comm, 13–14.
Julian et al., "Photoaddition of Olefins to Indoles ...," [1973] J.C.S. Chem Comm., 311–12.
Torii et al., "Electrochemical Acetoxylation of ...," J. Org. Chem. 43, 2882–85, (1978).
Abstract. Mutschter et al., Arch. Pharma. 311, 248–55, Chem Abstr. 89:24081r, (1978).
Ikeda, "Synthesis and Some Properties of IH-1-...," Tetrahedron Let, 21, 3403–06, (1980).
Hordlander et al., "Synthesis of Indoles from N- ...," J. Org. Chem. 46, 778–82, (1981).
Bass et al., "Tricyclic Amides: A New Class of ...," J. Agr. Food Chem. 29, 576–79, (1981).
Shafiee et al., "A Facile Method for Acylation ...," Synthesis, Comm. 389–90, (1981).
Abstract, Japanese Kokai 80/72162, Chem. Abstr. 94:103159d, (1981).

Primary Examiner—Richard L. Raymond
Assistant Examiner—D. B. Springer
Attorney, Agent, or Firm—Karl F. Jorda

[57] ABSTRACT

Indoles of the formula I which are unsubstituted in the 2- and 3-positions:

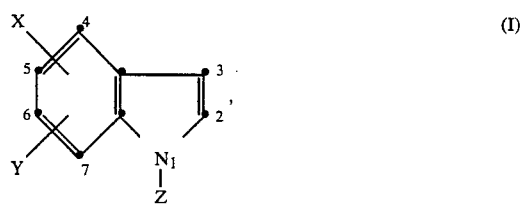

wherein Z is hydrogen or a group —COR, and X and Y have the meanings defined in claim 1, can be produced by a novel, simple and economical process which comprises reacting a compound of the formula II

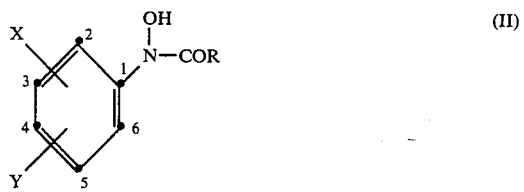

at a temperature of between 0° and 120° C., in the presence of a mercury or palladium catalyst, with benzoic acid vinyl ester, or with the vinyl ester of an aliphatic $C_1$–$C_4$-monocarboxylic acid; and optionally saponifying compounds of the formula I in which Z is —COR. The compounds of the formula I can be used for example for producing indigo dyes, or they can be used as pharmaceutical or agricultural active substances.

15 Claims, No Drawings

# PROCESS FOR PRODUCING INDOLES UNSUBSTITUTED IN THE 2,3-POSITION AND N(3-CHLOROPROPIONYL)INDOLE PRODUCED THEREBY

The invention relates to a novel process for producing indoles unsubstituted in the 2,3-position.

The best known indole syntheses [cp. for example "The Chemistry of Heterocyclic Compounds, Indoles", edited by A. Weissberger and E. C. Taylor, John Wiley, 1972] start with benzene derivatives substituted in the ortho-position by suitable functional substituents [cp. for example Mandelung and Reissert Indole Syntheses). The ortho-substitution of benzene derivatives causes however considerable difficulties, and even so it produces mixtures of ortho- and para-substituted benzene derivatives, so that consequently the starting products required for the said syntheses have to be firstly separated, by relatively involved means, from the corresponding para-substituted benzene derivatives [cp. for example: E. S. Gould, "Mechanismus und Struktur in der org. Chemie", Verlag Chemie, Weinheim, 1964, p. 517] (Mechanism and Structure in org. Chemistry). The economic efficiency of these methods is therefore unsatisfactory. Other known processes, such as the Fischer, Bischler and Japp-Klingemann indole syntheses, and the process described in the U.S. patent specification No. 3,564,009, are based on acid-catalysed rearrangement reactions, and some require high reaction temperatures. Since many indole derivatives are sensitive to acids and/or to heat, the yields obtained by these processes are not outstanding. Furthermore, the rearrangement reactions can be performed only with suitably substituted starting products (arylhydrazones, or ketones to be reacted with arylamines or with $N_1$-acyl-phenylhydrazones), which result in indoles substituted in the 2- and/or 3-position. Indoles which are unsubstituted in the 2- and 3-positions are not obtainable by these rearrangement reactions. Finally, N-trifluoroacetylindoles can be obtained also by reaction of N-(trifluoroacetyl)-anilinoacetals with excess trifluoroacetanhydride in boiling trifluoroacetic acid [cp. for example: J. Org. Chem., 46, 788–782 (1981)]. The anilinoacetals used for this purpose are however difficult to obtain. The indole formation proceeds moreover very slowly, and is limited to N-trifluoroacetyl derivatives.

The present invention relates to a novel simplified and economic process by which there can be produced, under mild reaction conditions and in high yields, indoles of the formula I unsubstituted in the 2- and 3-positions:

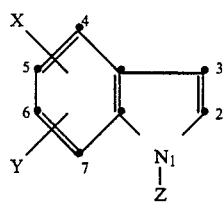

wherein
Z is hydrogen or a group —COR,
R is hydrogen, $C_1$-$C_4$-alkyl, $C_1$-$C_4$-alkoxy, $C_1$-$C_4$-haloalkyl, $C_2$-$C_4$-alkenyl, benzyl or phenyl,
X and Y independently of one another are each hydrogen, a halogen atom, $C_1$-$C_4$-alkyl, $C_1$-$C_4$-alkoxy, halomethyl, —OCO—$C_1$-$C_4$-alkyl, —CN, $NO_2$, —NH-CO—$C_1$-$C_4$-alkyl or phenyl, or together they are —CH=CH—CH=CH—, which is preferably bound in the 5,6-position, or X is bound in the 7-position, and together with R is —$CH_2CH_2$—, which process comprises reacting a compound of the formula II

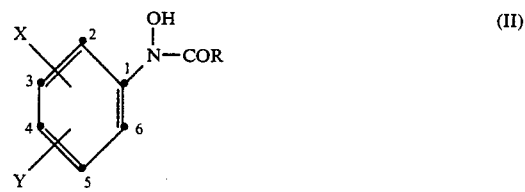

at a temperature of between 0° and 120° C., in the presence of a mercury or palladium catalyst, with a compound of the formula III

$$CH_2=Ch—OCOR'$$ (III)

wherein R, X and Y have the meanings defined under the formula I, and, when X and R together are —$CH_2CH_2$—, X is bound in the ortho-position with respect to the group —N(OH)—COR, and R' is $C_1$-$C_4$-alkyl or phenyl; and optionally saponifying compounds of the formula I in which Z is —COR (Z=H).

A further advantage of the process according to the invention is that uniformly N-acylated indoles are obtained by the process directly. This protective group is frequently advantageous or even essential for further reactions. Indoles which are N-acylated are generally produced by subsequent acylation of the corresponding N-unsubstituted indoles. When however the 3-position of the indole is unsubstituted, then also this position becomes partially or predominantly acylated, which renders necessary a later separation of the different products [cp. for example: Synthesis, Comm., 389 (1981)]. The stated protective group can if desired be easily removed by saponification.

Alkyl groups R', alkyl, alkoxy, haloalkyl and alkenyl groups R, alkyl and alkoxy groups X or Y or alkyl groups present in substituents X or Y can be straight-chain or branched-chain.

When X and/or Y are halogen atoms, or if substituents R, X and/or Y are substituted by halogen atoms, they are for example bromine atoms, particularly however they are fluorine atoms and especially chlorine atoms.

Examples of alkyl groups R', alkyl, alkoxy, haloalkyl or alkenyl groups R, and alkyl, alkoxy, halomethyl, —OCO—$C_1$-$C_4$-alkyl or —NHCO—$C_1$-$C_4$-alkyl groups X and/or Y which may be mentioned are: methyl, ethyl, n-propyl, isopropyl, n-butyl, sec-butyl; methoxy, ethoxy, n-propoxy, isopropoxy; —$CH_2Cl$, —$CH_2Br$, —$CHCl_2$, —$CCl_3$, —$CF_3$, —$CH_2CH_2Cl$, —$CH_2CH_2CH_2Cl$; —CH=$CH_2$, —CH=$CHCH_3$, —C($CH_3$)=$CH_2$; —OCO-methyl, —OCO-ethyl, —OCO-n-propyl, —OCO-isopropyl; —NHCO-methyl, —NHCO-ethyl, —NHCO-n-propyl and —NHCO-n-butyl.

Alkyl groups R', alkyl, alkoxy and haloalkyl groups R, as well as alkyl, alkoxy, —OCO-alkyl and —NHCO-alkyl groups X and/or Y preferably contain 1 or 2 C atoms in the alkyl group. Preferred alkenyl groups R are those having 3 and in particular 2 C atoms.

In the process according to the invention, there are preferably used on the one hand compounds of the formula II wherein R is hydrogen, $C_1$–$C_2$-alkyl, $C_1$–$C_2$-alkoxy, $C_1$–$C_2$-haloalkyl, vinyl or phenyl, X is hydrogen, and Y is hydrogen, chlorine or $C_1$–$C_2$-alkyl, especially compounds of the formula II wherein R is methyl, —CH$_2$Cl, —CH$_2$CH$_2$Cl or vinyl, and X and Y are hydrogen.

Preferably used on the other hand in the process according to the invention are compounds of the formula II wherein X and R together are —CH$_2$CH$_2$—, and Y is hydrogen, a halogen atom, $C_1$–$C_4$-alkyl, $C_1$–$C_4$-alkoxy, —OCO—$C_1$–$C_4$-alkyl or —CN, particularly hydrogen, chlorine or $C_1$–$C_2$-alkyl, and more especially preferred is hydrogen.

Vinylacetate is preferably used as compound of the formula III.

The reaction according to the invention is advantageously performed in the presence of an inert organic solvent. Suitable organic solvents are for example: optionally halogenated, aromatic or aliphatic, hydrocarbons, such as benzene, toluene, xylenes, chlorobenzene, dichlorobenzenes, n-pentane, n-hexane, n-heptane, chloroform, dichloromethane or dichloroethane; aliphatic and cyclic ethers, such as dialkyl ethers having 1 to 4 C atoms in each of the alkyl moieties, for example diethyl ether, di-n-propyl ether and di-isopropyl ether, tetrahydrofuran, tetrahydropyrane and dioxane; alkyl- and alkoxy esters of aliphatic monocarboxylic acids having in all 2 to 6 C atoms, such as formic acid-methyl and -ethyl esters, acetic acid-methyl-, -ethyl, -n-butyl and -isobutyl esters; alkylnitriles, especially those having 2 to 5 C atoms, such as acetonitrile, propionitrile and butyronitrile; benzonitrile; aliphatic ketones preferably having in all 3 to 8 C atoms, such as acetone, diethyl ketone, methylisopropyl ketone, diisopropyl ketone or methyl-tert-butyl ketone; amides, such as N,N-dialkylamides of aliphatic monocarboxylic acids having 1 to 3 C atoms in the acid moiety moiety, for example N,N-dimethylformamide, N,N-dimethylacetamide, N,N-diethylacetamide; and hexamethylphosphoric acid triamide (Hexametapol).

The preferred solvent is an excess of the compound of the formula III, especially excess vinylacetate.

The reaction temperatures are advantageously between 20° and 75° C., especially between 50° and 75° C. The reaction can be carried out under normal pressure, or under elevated pressure, for example up to about 10 bar. The reaction is usually performed under normal pressure.

The mercury catalysts used are for example: mercury acetate, mercury(II) bromide, -chloride or -iodide, mercury(I) chloride and -iodide, mercury(II) cyanide, mercury(I) or -(II) nitrate and mercury(II) thiocyanate. Mercury acetate is preferred. Particularly preferred are however palladium catalysts, such as palladium metal, for example compounds of the formula IV $$M^y[PdL_n]^x \quad (IV)$$

wherein n is an integer from 2 to 4, x is $2\oplus$ to $2\ominus$, y= —(x), M, where x is not equal to nought, is an ion of opposite charge, and the L's are identical or different phosphorus-free ligands, for example Cl, Br, J, —CN, —NO$_3$, $C_1$–$C_{12}$-alkyl-COO,

CH$_3$COCHCOCH$_3$,
|

NH$_3$, 2,2'-bipyridyl, o-phenanthroline,

OS(CH$_3$)$_2$
| or —NC-phenyl. Suitable compounds of the formula IV are for example: PdCl$_2$, PdBr$_2$, Pd(CN)$_2$, Pd(NO$_3$)$_2$, Pd(O$_2$C—$C_{1-12}$-alkyl)$_2$, especially Pd(OOCCH$_3$)$_2$, Pd(CH$_3$COCHCOCH$_3$)$_2$,
|

[Pd(NH$_3$)$_4$]Cl$_2$, [PdCl$_4$]Na$_2$, (PdCl$_4$)Li$_2$, Pd(OOCCH$_3$)$_2$(2,2'-bipyridyl), Pd(OOCCH$_3$)$_2$-(o-phenanthroline), PdCl$_2$[OS(CH$_3$)$_2$]$_2$
| and PdCl$_2$(NC-phenyl)$_2$.

For the reaction according to the invention, it is possible to use for example also palladium complexes of the type described in the U.S. patent specification No. 3,922,299, particularly complexes of Pd(OOC-$C_1$–$C_{12}$-alkyl)$_2$, especially palladium acetate, with trivalent phosphorus or arsenic compounds, such as trialkyl-, triaryl-, trialkoxy-, triphenoxy- or trihalophosphines or -arsines, or variably substituted trivalent phosphorus or arsenic compounds. The following may be mentioned as examples of such phosphorus or arsenic compounds: triphenylarsine, diphenylmethylphosphine, diphenylmethoxyphosphine, trimethylphosphine, triethylphosphine, tri-n-butylphosphine, triphenylphosphine, phenyl-di-n-butoxyphosphine, phosphorus trichloride, phenyldichlorophosphine and tri-o-tolylphosphine. The stated complexes can be used as such, or can be formed in situ, that is to say, in the reaction medium. It is possible to use, in addition to the above-mentioned compounds, also palladium compounds of other oxidation stages, for example bis-(dibenzylideneacetone)palladium(O) and bis(isonitrile)palladium(O) compounds. Examples of such isonitriles are: bis-(cyclohexylisonitrile)-palladium(O), bis-(isopropylisonitrile)palladium(O), bis-(tert-butylisonitrile)palladium(O), bis-(p-tolylisonitrile)palladium(O), bis-(phenylisonitrile)palladium(O) and bis-(p-methoxyphenylisonitrile)-palladium(O).

The catalyst particularly preferably used is Li$_2$PdCl$_4$.

The catalysts are used generally in an amount of 0.001 to 20 mol %, preferably 0.01 to 3 mol %, relative to the compound of the formula II.

The possible saponification of compounds of the formula I where Z=—COR to obtain compounds of the formula I where Z=H can be performed, in a manner known per se, in an alkaline medium, advantageously with the use of KOH or NaOH in aqueous methanol. The indoles of the formula I obtained according to the invention can moreover if desired be catalytically hydrogenated to the corresponding indolines, for example by a method analogous to that described in Acta Chim. Acad. Sci. Hung., 67, 229–239 (1971). Compounds of the formula I which are particularly suitable for this catalytic hydrogenation are those wherein Z is —COR. The compounds of the formula I and the indolines obtainable therefrom, so far as they are novel, likewise form subject matter of the present invention.

The starting products of the formulae II and III are known, or they can be produced by methods known per se. Compounds of the formula II can be produced for example by reaction of the N-phenylhydroxylamines with the corresponding acyl chlorides in the presence of $NaHCO_3$ as base.

Compounds of the formula I wherein X and R together do not form a ring are suitable for example for the production of indigo dyes [cp. for example J. Org. Chem., 43. 2882 (1978)]. Compounds of the formula I and/or the indolines obtainable therefrom, particularly those wherein X is bound in the 7-position and together with R is —$CH_2CH_2$— are also used as pharmaceutical or agricultural active substances, for example as herbicides, fungicides or bactericides, or they are valuable starting products for producing biologically active substances [cp. for example: J. Agric. Food Chem., 29. 576-579 (1981); British patent specification No. 1,394,373; Japanese Published specification No. 80/72162, reported in CA, 94, 103159d (1981); CA, 89, 24081r (1978); and U.S. Pat. No. 3,564,009]. Certain N-acylindoles are suitable also for photochemical cycloaddition reactions [cp. for example: J.C.S. Chem. Comm., 13 (1973) and 311 (1973), and also Tetrahedron Letters, 21, 3403 (1980)].

EXAMPLE 1

50 g (0.25 mol) of N-hydroxy-N-($\beta$-chloropropionyl)-aniline are placed into 200 ml of vinyl acetate, and 1 g of $Li_2PdCl_4$ is added. The reaction mixture is stirred at 60° C. for 4 hours, and is then washed with brine and concentrated by evaporation. The solid residue is recrystallised from diethyl ether/n-hexane to thus obtain 43.1 g (83% of theory) of N-(3-chloropropionyl)indole, m.p. 67° C.; IR spectrum ($CHCl_3$): 1705 (CO): NMR spectrum (100 MHz, $CDCl_3$): 3.27 and 3.91 (for each t, J is in each case 7; in each case $CH_2$); 6.60 (d, J=4, CH); 7.81-7.60 (m, 4H); 8.47-8.38 (m, CH) ppm. The N-(3-chloropropionyl)-indole is novel.

The employed N-hydroxy-N-($\beta$-chloropropionyl)-aniline is produced as follows: 150 g (1.38 mols) of phenylhydroxylamine, 151 g (1.8 mols) of $NaHCO_3$ and 550 ml of ethyl acetate are placed at 0° C. into the reaction vessel. There are then added dropwise, within one and a half hours, 173.4 g (1.38 mols) of $\beta$-chloropropionyl chloride in 150 ml of ethyl acetate. After removal of the ice bath, stirring is maintained for 2 hours. The reaction mixture is then filtered (NaCl), washed, and concentrated by evaporation; and the solid residue is treated with a small amount of diethyl ether. The yield is 261.2 g (95% of theory) of N-hydroxy-N-($\beta$-chloropropionyl)-aniline in the form of a white crystalline powder, m.p. 87°-88° C. The starting products of the formula II which are used in the following Examples 2 to 4 and 6 to 11 are known, or can be produced by methods analogous to known methods.

EXAMPLE 2

In a manner analogous to that of Example 1, 3.1 g of N-hydroxy-N-formylaniline, 200 mg of $Li_2PdCl_4$ and 60 ml of vinyl acetate are reacted at 55° C. for 6 hours, and, after further processing, N-formylindole is obtained; IR spectrum ($CHCl_3$): 1660 (CO): NMR spectrum (100 MHz, $CDCl_3$): 6.54 (broad d, J=5 Hz, CH); 7.0-7.3 (m, 4H); 8.02 (broad d, J=6 Hz, CH); 8.68 (s, $\underline{H}$—CO) ppm.

EXAMPLE 3

30.0 g of N-acetyl-N-hydroxyaniline, 2 g of $Li_2PdCl_4$ and 400 ml of vinyl acetate are stirred for 5 hours at 50° to 55° C. The dark reaction solution is concentrated by evaporation, and in toluene/ethyl acetate (4:1) is filtered through a small amount of silica gel. The yield after concentration of the filtrate by evaporation is 28.9 g of yellow oily N-acetylindole, b.p. 146°-149° C./1600 Pa; IR spectrum ($CHCl_3$): 1710 (CO): NMR spectrum (100 MHz, $CDCl_3$): 2.77 (s, $CH_3$); 6.77 (d, J=4, CH); 7.3-7.8 (m, 4H); 8.6 (m, 1H) ppm.

EXAMPLE 4

A solution of 12.0 g of N-methoxycarbonyl-N-hydroxyaniline in 120 ml of vinyl acetate is stirred with 200 mg of $Li_2PdCl_4$ for 7 hours at 60° C.; it is then washed with brine, dried over magnesium sulfate and concentrated by evaporation. Chromatography through silica gel (toluene/ethyl acetate 4:1) yields 7.3 g of N-methoxycarbonylindole as colourless oil; IR spectrum ($CHCl_3$): 1730 (CO): NMR spectrum (60 MHz, $CDCl_3$): 1.47 (t, J=7, $CH_3$); 4.47 (q, J=7, $CH_2$); 6.53 (d, J=3.5, CH); 7.1-7.7 (m, 4H); 8.13 (m, 1H) ppm. 1.4 g of an O-acetylated educt in the form of yellow oil are obtained as a second fraction of chromatography.

EXAMPLE 5

10.0 g of N-hydroxy-2-oxo-1,2,3,4-tetrahydroquinoline [produced according to J. Pharm. Pharmacol. 16, 773 (1964)], 100 ml of vinyl acetate and 0.5 g of $Li_2PdCl_4$ are stirred at 60° C. for 2 hours. The reaction mixture is subsequently washed with brine, dried over magnesium sulfate, and concentrated by evaporation. The residue is chromatographed through silica gel (toluene/ethyl acetate 1:1) to thus obtain crystalline 5,6-dihydro-4H-pyrrolo-[3,2,1-i,j]-quinolin-4-one, m.p. 102°-104° C.; IR spectrum ($CHCl_3$): 1720 (CO): NMR spectrum (100 MHz, $CDCl_3$) 2.7 (m, 2H); 2.95 (m, 2H); 6.46 (d, J=4, CH); 6.8-7.3 (m, 3H); 7.47 (d, J=4, CH) ppm.

EXAMPLE 6

8.3 g of N-hydroxybenzanilide are heated with 125 ml of vinyl acetate and 250 mg of $Li_2PdCl_4$ for four and a half hours at 60° C. The reaction mixture is washed with brine, dried over magnesium sulfate, and concentrated by evaporation. The solid residue is shaken with diethyl ether, in the process of which a small amount of crystalline benzanilide precipitates. The organic phase is concentrated by evaporation, and chromatographed through silica gel (toluene/diethyl ether 1:1). As the first fraction are obtained 6.2 g of N-benzoylindole, m.p. 54°-55° C.; IR spectrum ($CHCl_3$): 1710 (CO): NMR spectrum (100 MHz, $CDCl_3$) 6.52 (d, J=4, CH); 7.1-7.7 (m, 9H); 8.38 (m, 1H) ppm.

EXAMPLE 7

26.0 g of N-hydroxy-acrylanilide are stirred in 250 ml of vinyl acetate, in the presence of 0.5 g of $Li_2PdCl_4$, for 4 hours at 50° C. The reaction mixture is decanted from resinous constituents, and then concentrated by evaporation. The residue is filtered through silica gel (diethyl ether/cyclohexane 1:1). The filtrate is concentrated by evaporation, and is brought to crystallisation with a small amount of diethyl ether. The yield is 20.1 g of N-acryloylindole, m.p. 46°–48° C.; IR spectrum (CHCl₃: 1690 (CO): NMR spectrum (100 MHz, CDCl₃): 5.95 (X part of ABX, J=2 and 10, CH); 6.5-7.1 (AB of ABX, with J=2, 10 and 16, CH₂ as well as d, J=3, CH); 7.2-7.6 (m, 4H); 8.5 (m, CH) ppm.

EXAMPLE 8

31.6 g of N-hydroxy-chloroacetylanilide, 300 ml of vinyl acetate and 0.3 g of Li₂PdCl₄ are refluxed for 8 hours. The reaction mixture is concentrated by evaporation, and subsequently chromatographed through silica gel (toluene/ethyl acetate 1:1). Two fractions are obtained, the first consisting of crystalline N-chloroacetylindole, (m.p. 110°-112° C.; IR spectrum (KBr): 1705 (CO): NMR spectrum (100 MHz, DMSO-d₆) 5.02 (s, CH₂); 6.72 (d, J=4, CH); 7.1-7.7 (m, 3H); 7.79 (d, J=4, CH); 8.3 (m, 1H) ppm.

The second fraction consists of N-chloroacetyl-2-hydroxyindoline (m.p. 121°-122° C.), which can be converted by means of KHSO₄ in boiling toluene, with elimination of water, into the indole derivative.

EXAMPLE 9

1.0 g of N-hydroxy-N-acetyl-2-chloroaniline, 15 ml of vinyl acetate and 20 mg of Li₂PdCl₄ are stirred at 60° C. for 6 hours. The reaction mixture is then cooled, washed with water, dried over magnesium sulfate, and concentrated by evaporation. The residue is caused to crystallise from a small amount of diethyl ether and there is thus obtained N-acetyl-7-chlorindole in the form of beige crystals, m.p. 81°-83° C.; IR spectrum (CHCl₃) 1750 (CO): NMR spectrum (100 MHz, CDCl₃): 2.70 (s, CH₃); 6.63 (d, J=4, CH); 7.1-7.6 (m, 4H) ppm.

EXAMPLE 10

1.2 g of N-hydroxy-N-acetyl-4-methylaniline, 12 ml of vinyl acetate and 50 mg of Li₂PdCl₄ are stirred at 60° C. for 8 hours. The reaction mixture is washed with brine, dried with magnesium sulfate, and concentrated by evaporation. The residue (dark oil) is caused to crystallise with diethyl ether/n-hexane to thus obtain N-acetyl-5-methylindole as beige powder, m.p. 56°-58° C.; IR spectrum (CHCl₃) 1720 (CO): NMR spectrum (100 MHz, CDCl₃: 2.45 (s, CH₃); 2.61 (s, CH₃); 6.55 (d, J=4, CH); 7.1-7.4 (m, 3H); 8.3 (m, 1H) ppm.

EXAMPLE 11

2.1 g of N-hydroxy-N-acetyl-3-methylaniline, 25 ml of vinyl acetate and 70 mg of Li₂PdCl₄ are stirred at 60°-65° C. for four and a half hours. The reaction mixture is washed with brine, dried with magnesium sulfate, and concentrated by evaporation. The residue, a viscous substance, is chromatographed through silica gel (toluene/ethyl acetate 1:2) to thus obtain a 1:1 mixture of the N-acetyl-4- and -5-methylindoles; IR spectrum (CHCl₃): 1725 (CO): NMR spectrum (100 MHz, CDCl₃): 2.36 and 2.43 (for each s, in each case CH₃); 6.38 and 6.45 (for each d, in each case J is 4, CH); 6.9-7.4 (m, 3H); 8.2 (m, 1H) ppm.

EXAMPLE 12

13.1 g of N-acetylindole are introduced into a solution of 3.7 g of NaOH, 75 ml of methanol and 37 ml of water, and the mixture is stirred for 4 hours at room temperature. The methanol is subsequently distilled off, and the intensively concentrated reaction mixture is subjected to steam distillation. The yield is 7.7 g of slightly yellow indole as scaly crystals, m.p. 50°-52° C.

EXAMPLE 13

10.4 g of N-(β-chloropropionyl)-indole are hydrogenated in 150 ml of methanol, with the use of 1 g of Pd/C (5% by weight of Pd) at room temperature and under normal pressure. Hydrogenation is terminated after 1 hour (hydrogen absorption=102% of theory). The catalyst is filtered off, and the reaction product is subsequently washed with a large amount of ethyl acetate, the filtrate then being concentrated by evaporation. The yield is 10.2 g of N-(β-chloropropionyl)-indoline in the form of white powder, m.p. 87°-88° C.; IR spectrum (CHCl₃): 1665 (CO): NMR spectrum (100 MHz, CDCl₃): 2.75 (t, J=7, CH₂); 3.06 (t, J=7, CH₂); 3.76 (t, J=7, CH₂); 3.88 (t, J=7, CH₂); 6.8-7.2 (m, 3H); 8.15 (m, 1H) ppm.

EXAMPLE 14

The procedure is carried out as in Example 1 except that 3 g of mercury acetate are used as catalyst instead of 1 g of Li₂PdCl₄. After the reaction mixture has been refluxed for 48 hours, it is washed with brine and dried over magnesium sulfate. The crude product, concentrated by evaporation, is chromatographed through silica gel (toluene/ethyl acetate 4:1). The first fraction yields slightly yellow crystals of N-(β-chloropropionyl-)indole, m.p. 66°-67° C.

What is claimed is:

1. A process for producing a compound of the formula I

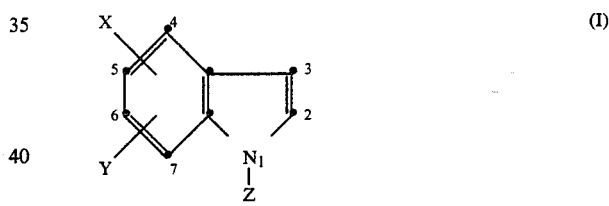

wherein
Z is hydrogen or a group —COR,
R is hydrogen, C₁-C₄-alkyl, C₁-C₄-alkoxy, C₁-C₄-haloalkyl, C₂-C₄-alkenyl, benzyl or phenyl,
X and Y independently of one another are each hydrogen, a halogen atom, C₁-C₄-alkyl, C₁-C₄-alkoxy, halomethyl, —OCO—C₁-C₄-alkyl, —CN, —NO₂, —NHCO—C₁-C₄-alkyl or phenyl,
which process comprises reacting a compound of the formula II

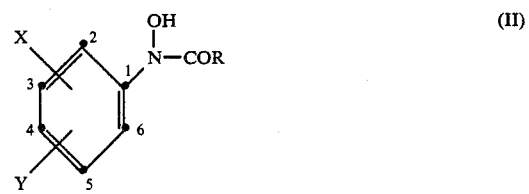

at a temperature of between 0° and 120° C., in the presence of a mercury or palladium catalyst, with a compound of the formula III

wherein R, X and Y have the meanings defined under the formula I, and, when X and R together are —CH₂CH₂—, X is bound in the ortho position with respect to the group —N(OH)—COR, and R' is $C_1$-$C_4$-alkyl or phenyl; and optionally saponifying a compound of the formula I in which Z is —COR to a compound of the formula I wherein Z is H.

2. A process according to claim 1, wherein there is used a compound of the formula II in which R is hydrogen, $C_1$-$C_2$-alkyl, $C_1$-$C_2$-alkoxy, $C_1$-$C_2$-haloalkyl, vinyl or phenyl, X is hydrogen, and Y is hydrogen, chlorine or $C_1$-$C_2$-alkyl.

3. A process according to claim 1, wherein there is used a compound of the formula II in which R is methyl, —CH₂Cl, —CH₂—CH₂Cl or vinyl, and X and Y are hydrogen.

4. A process according to claim 1, wherein there is used a compound of the formula 11 in which X and R together are —CH₂CH₂—, and Y is hydrogen, a halogen atom, $C_1$-$C_4$-alkyl, $C_1$-$C_4$-alkoxy, —OCO—$C_1$-$C_4$-alkyl or —CN.

5. A process according to claim 1, wherein there is used a compound of the formula II in which X and R together are —CH₂CH₂—, and Y is hydrogen, chlorine or $C_1$-$C_2$-alkyl.

6. A process according to claim 1, wherein there is used a compound of the formula II in which X and R together are —CH₂CH₂—, and Y is hydrogen.

7. A process according to claim 1, wherein vinyl acetate is used as the compound of the formula III.

8. A process according to claim 1, wherein the reaction is performed in an inert organic solvent.

9. A process according to claim 1, wherein the reaction is performed in excess compound of the formula III, particularly in excess vinyl acetate.

10. A process according to claim 1, wherein the reaction is performed at a temperature of between 20° and 75° C.

11. A process according to claim 1, wherein a palladium catalyst is used.

12. A process according to claim 1, wherein the catalyst used is palladium metal or a compound of the formula IV $$M^y[PdL_n]^x \qquad (IV)$$

wherein n is an integer from 2 to 4, x is $2\oplus$ to $2\ominus$, y is —(x), M, where x is not equal to nought, is an ion of opposite charge, and the L's are identical or different phosphorus-free ligands.

13. A process according to claim 1, wherein Li₂PdCl₄ is used as the catalyst.

14. A process according to claim 1, wherein the catalyst is used in an amount of 0.01 to 3 mol %, relative to the compound of the formula II.

15. N-(3-Chloropropionyl)-indole.

* * * * *